(12) United States Patent
Park et al.

(10) Patent No.: US 7,527,803 B2
(45) Date of Patent: *May 5, 2009

(54) PLGA SUBSTRATE WITH ALIGNED AND NANO-SIZED SURFACE STRUCTURES AND ASSOCIATED METHOD

(75) Inventors: Grace E. Park, West Lafayette, IN (US); Brian C. Ward, Brownsburg, IN (US); Kinam Park, West Lafayette, IN (US); Thomas J. Webster, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/793,721

(22) Filed: Mar. 5, 2004

(65) Prior Publication Data

US 2004/0214322 A1    Oct. 28, 2004

Related U.S. Application Data

(63) Continuation-in-part of application No. 10/634,292, filed on Aug. 5, 2003.

(60) Provisional application No. 60/452,847, filed on Mar. 7, 2003, provisional application No. 60/401,060, filed on Aug. 5, 2002, provisional application No. 60/312,800, filed on Aug. 16, 2001.

(51) Int. Cl.
    *C12N 5/06* (2006.01)

(52) U.S. Cl. ............. 424/400; 424/93.1; 977/755; 977/828; 435/395

(58) Field of Classification Search ........... 435/325, 435/395, 363; 424/400, 93.1, 93.7; 977/755, 977/828

See application file for complete search history.

(56) References Cited

U.S. PATENT DOCUMENTS

6,270,347 B1 *   8/2001   Webster et al. ............. 433/173
6,805,898 B1    10/2004   Wu et al.
2002/0173033 A1 * 11/2002   Hammerick et al. ..... 435/305.2

OTHER PUBLICATIONS

J. Black and G. Hastings, "Handbook of Biomaterial Properties", *Chapman & Hall*, pp. 40-47 (1998).

Mankin et al., "Orthopaedic Basic Science—Chapter 1 Form and Function of Articular Cartilage", *American Academy of Orthopaedic Surgeons*, pp. 1-45, (1994).

Mikos et al., "Preparation and characterization of poly(L-lactic acid) foams", *Polymer*, vol. 35, No. 5, pp. 1068-1077, (1994).

Kay et al., "Nanostructured Polymer/Nanophase Ceramic Composites Enhance Osteoblast and Chondrocyte Adhesion", *Tissue Engineering*, vol. 8, No. 5, pp. 753-761, (2002).

Thapa et al., "An Investigation of Nano-structured Polymers for Use as Bladder Tissue Replacement Constructs", *Mat. Res. Soc. Symp. Proc.*, vol. 711, pp. 205-210, (2002).

Miller et al., An In Vitro Study of Nano-fiber Polymers for Guided Vascular Regeneration, *Mat. Res. Soc. Symp. Proc.*, vol. 711, pp. 201-204, (2002).

Jun et al., "An In Vitro Study of Chondrocyte Function on Nanostructured Polymer/Ceramic Formulations to Improve Cartilage Repair", *Nano 2002* Conference Abstract Book, Orlando, FL, p. 269, (2002).

* cited by examiner

*Primary Examiner*—Ruth A Davis
(74) *Attorney, Agent, or Firm*—Barnes & Thornburg LLP

(57) ABSTRACT

A substrate for promoting growth of chondrocytes to repair articular cartilage is disclosed. The substrate comprises a polymeric material comprising aligned and nano-sized surface structures. An associated method is disclosed.

12 Claims, 5 Drawing Sheets alignment direction alignment direction

Bar= 100μm

PLGA SUBSTRATE WITH ALIGNED AND NANO-SIZED SURFACE STRUCTURES AND ASSOCIATED METHOD

CROSS-REFERENCE TO RELATED APPLICATIONS

This application claims priority to U.S. Provisional Patent Application No. 60/452,847 filed on Mar. 7, 2003 and claims priority as a continuation-in-part to U.S. patent application Ser. No. 10/634,292 filed on Aug. 5, 2003, the disclosures of which are hereby incorporated by reference herein. U.S. patent application Ser. No. 10/634,292 claims priority to U.S. Provisional Patent Application No. 60/401,060 which was filed on Aug. 5, 2002 and is hereby incorporated by reference herein. Cross reference is made to international application number PCT/US02/25812 which was filed on Aug. 14, 2002, is hereby incorporated by reference herein, and claims the benefit of U.S. Provisional Patent Application No. 60/312,800 which was filed on Aug. 16, 2001 and is hereby incorporated by reference herein.

GOVERNMENT RIGHTS

Research relating to the present application was supported by the U.S. Government under National Science Foundation Grant No. DGE-99-72770. The U.S. Government may have certain rights in this application.

FIELD

This application relates to substrates for promoting tissue growth.

BACKGROUND

Articular cartilage provides joints with excellent friction, coating, and wear properties necessary for knee movement, such as constant gliding. Articular cartilage consists of extracellular matrix (composed of collagen, poteoglycans, and water) and chondrocytes (cartilage-synthesizing cells). Collagen fibers in cartilage are aligned and generally have thin diameters, ranging from 10 nm to 100 nm, becoming thick (however, still in the nanometer regime) with age and disease (reference is made to Parsons J R, "Cartilage," In: Black J, Hastings G, editors, *Handbook of Biomaterial Properties*, Chapman and Hall, London: 1998, 40, the disclosure of which is hereby incorporated by reference herein). Articular cartilage has a limited capacity for repair when the tissue is damaged or diseased (reference is made to Mankin H J, et al., "Metabolism of Articular Cartilage," In: Simon S P, et al., editors, *Form and Function of Bone in Orthopaedic Basic Science*, American Academy of Orthopaedic Surgeons, Columbus, Ohio: 1994, 12, the disclosure of which is hereby incorporated by reference herein). This limited self-regeneration capability has made it difficult to create successful cartilage-tissue engineered replacements.

SUMMARY

A substrate for promoting growth of chondrocytes to repair articular cartilage is disclosed. The substrate comprises a polymeric material comprising aligned and nano-sized surface structures.

The polymeric material comprises, for example, poly (lactic/glycolic acid) material. Aligned ridges are formed on the surface by stretching the poly (lactic/glycolic acid) material. The substrate is etched with a compound (e.g., NaOH) to form the nano-sized surface structures.

BRIEF DESCRIPTION OF THE DRAWINGS

FIG. 1a shows non-aligned, conventional PLGA;
FIG. 1b shows aligned, conventional PLGA;
FIG. 1c shows non-aligned, nano-structured PLGA;
FIG. 1d shows aligned, nano-structured PLGA.

DETAILED DESCRIPTION

In the present study, bioresorbable poly (lactic/glycolic acid) (PLGA) materials with modified surface characteristics were tested as scaffolds to enhance chondrocyte (cartilage-synthesizing cells) adhesion and proliferation. Nano-dimensional features were aligned on the PLGA surfaces to simulate the physiological structure of articular cartilage. Nanostructured PLGA topographical features were created by etching the surface with 10N NaOH for 1 hour. Alignment was created by mechanically stretching the etched PLGA longitudinally at 60% strain while curing. The results showed decreased chondrocyte numbers on nano-dimensional substrates after 4-hour adhesion experiments. However, higher cell densities were observed on nano-dimensional substrates after 1, 3, and 6 days during proliferation experiments, indicating for the first time that chondrocytes proliferated at a faster rate on the nanostructured substrates. Furthermore, migration studies using TEFLON® (i.e., polytetraflouroethylene) fences demonstrated longer distances of preferential alignment of chondrocytes along aligned nanostructured PLGA ridges after 2, 4, and 6 days. The present study thus provided the first evidence that mimicking the topographical structure of articular cartilage by aligning nanometer surface features on PLGA will enhance chondrocyte proliferation needed for articular cartilage restoration.

The overall objective of this study was to develop a biodegradable implant that mimics collagen structure and dimension to enhance the adhesion and growth of chondrocytes and thus promote regeneration of cartilage. More specifically, inducing alignment of surface features on scaffold materials coupled with increasing nano-dimensional surface roughness may simulate the environment chondrocytes experience in situ. In this study, chondrocyte adhesion, proliferation, and migration distances were determined on aligned nanostructured poly(lactic-co-glycolic acid) (PLGA) substrates.

MATERIALS AND METHODS

Substrate Preparation

Figure 5:
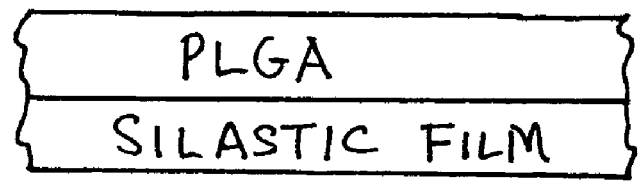
FIG. 5 is a diagrammatic view showing a layer of PLGA formed on a layer of silastic film.
Figure 6:
FIG. 6 is a diagrammatic view showing stretching of the PLGA to form aligned ridges on the surface of the PLGA.
Figure 7:
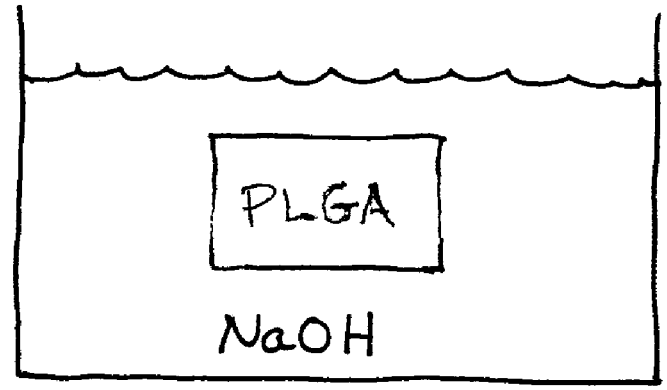
FIG. 7 is a diagrammatic view showing treatment of the PLGA with a compound such as NaOH to form nano-sized structures on the surface of the PLGA.

Poly (lactic/glycolic acid) (PLGA; 50:50 wt %; Polysciences, Inc.) copolymer films were synthesized using chloroform and heat treatment according to standard techniques [reference is made to Mikos A, Thorsen A, Czerwonka L, Boa Y, Winslow D, Vancanti J, and Langer R, "Preparation and Characterization of Poly(L-lactic) Foams for Cell Transplantation,", *Polymer* 1990; 35:1068, the disclosure of which is hereby incorporated by reference herein]. The copolymer solution (0.25 g PLGA in 2 mL chloroform) was poured onto a silastic film (7 cm×3.5 cm×1 mm), as suggested, for example, in FIG. 5, and strained by 60% using clamps, as suggested, for example, in FIG. 6; this induced aligned ridges on the PLGA surface. The copolymer assembly was covered with parafilm; air-dried overnight at room temperature and placed in a vacuum (at 15-in Hg pressure) for 48 hours to allow chloroform to evaporate. Samples of PLGA (1 cm×0.5 cm×0.05 cm) were cut from the bulk polymer film for use in all experiments. Some polymer scaffolds of PLGA were soaked for 1 hour in 10N NaOH at room temperature to create nano-structured (surface features less than 100 nm) substrates, as suggested, for example, in FIG. 7. Unmodified PLGA (processed the same way except for NaOH treatment) served as conventional (i.e., control) PLGA substrates. Borosilicate glass coverslips etched with 1N NaOH, sterilized by autoclaving, were used as reference substrates.

Surface Characterization

Surface topography and roughness of the substrates were evaluated using scanning electron microscopy (JOEL JSM-840). Samples were coated with gold via a sputter-coater at ambient temperature. Micrographs were taken at 250× with 5-7 kV.

Cytocompatibility

Human chondrocytes (PN=6-12; Cell Applications, Inc.) were cultured using chondrocyte growth media (Cell Applications, Inc.) under standard cell culture conditions (i.e., a 37° C., humidified, 5% $CO_2$/95% air environment). For proliferation experiments, human chondrocytes were seeded at a density of 5,000 cells/$cm^2$ onto each substrate and incubated under standard cell culture conditions in chondrocyte growth media for 1, 3 and 6 days. Chondrocyte growth media was replaced every other day. Adhesion experiments were performed under similar conditions as proliferation, except cells were cultured for only 4 hours. At the end of each time period, the cells were fixed with 4% formaldehyde and stained with Coomassie Blue. The cells were counted at five random fields on each substrate using a brightfield light microscope, and these numbers were averaged and reported as cell density or cells/$cm^2$. All experiments were done in duplicate, and repeated at least three separate times.

Chondrocyte migration was investigated on the substrates of interest to determine whether the surface features on the substrates would influence chondrocytes to align as they migrate. TEFLON® inserts with rectangular well (0.6 cm×0.3 cm), off center from the insert, were employed to trap the cells and to give them a starting line for migration. These inserts and 2 mL chondrocyte growth media were placed into the 12-well plate, and 50,000 chondrocytes were micropipetted into the small well created by the TEFLON® insert. The TEFLON® fences covered the entire substrate surface except for a rectangular area. Cells were allowed to adhere for 4 hours, and the inserts were removed carefully. Free-floating cells were aspirated off and the media was replaced. Then the cells were free to migrate for 2, 4, and 6 days under standard cell culture conditions. Growth media was replaced every other day. After each incubation period, cells were fixed with 3.7% formaldehyde, stained with Coomassie Blue and migration distance determined by light microscopy at 10×.

Statistical Analysis

Data were analyzed using standard Student t tests with $p<0.05$ indicating statistical significance.

RESULTS

Substrate Characterization

Figure 1A:
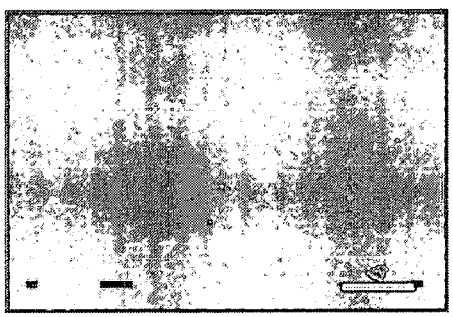
FIGS. 1a-1d show scanning electron micrographs of PLGA substrates.
Figure 1B:
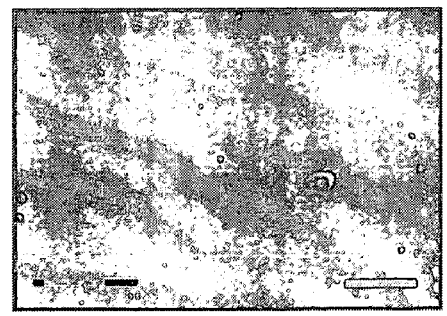
Figure 1C:
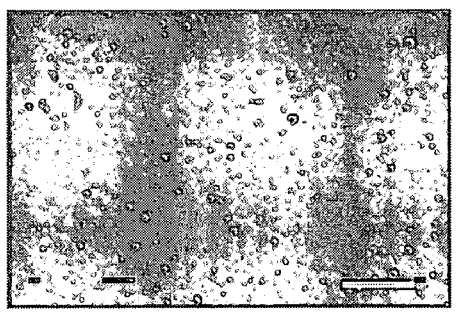
Figure 1D:
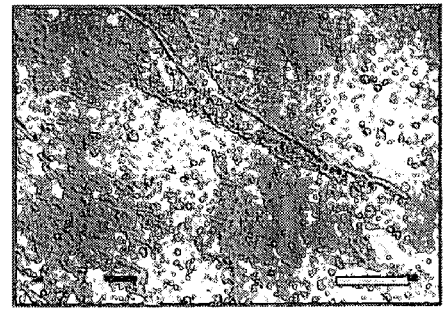

Scanning electron microscope (SEM) images provided evidence that surface features were aligned (indicated by arrows) by using strain (FIG. 1*b* compared to FIG. 1*a* and FIG. 1*d* compared to FIG. 1*c*). Moreover, treating PLGA with NaOH created nanostructured surface features (FIG. 1*c* compared to FIG. 1*a* and FIG. 1*d* compared to FIG. 1*b*).

Chondrocyte Interaction with Substrates

Figure 2:
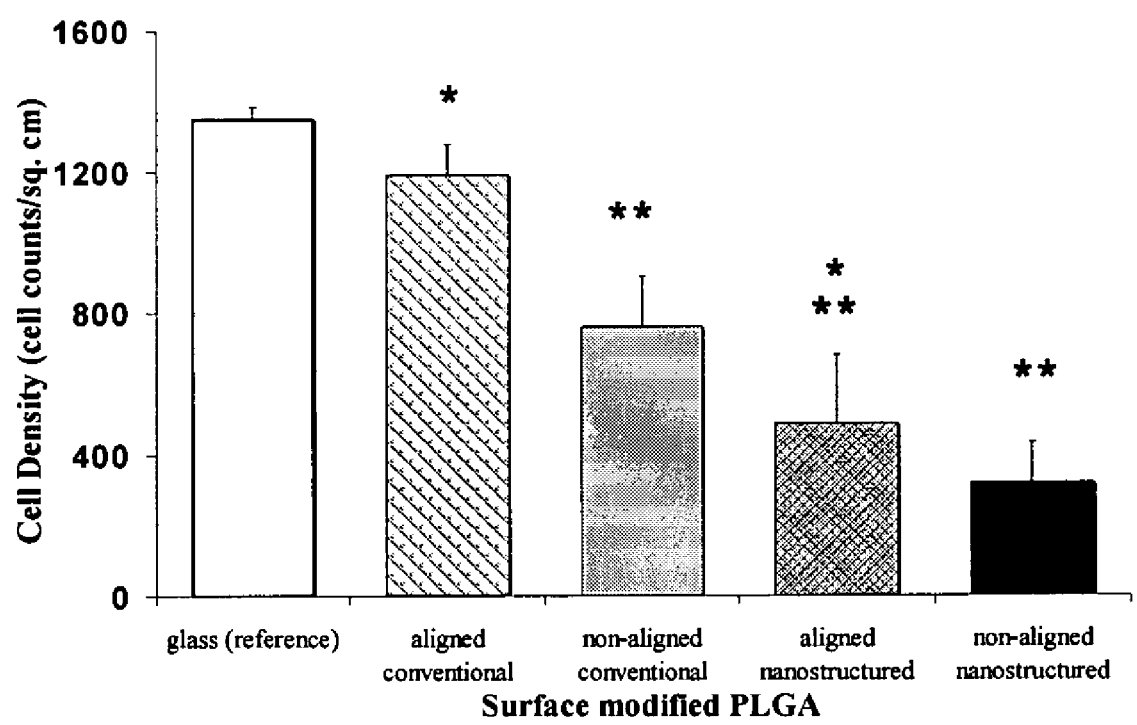
FIG. 2 shows four-hour chondrocyte adhesion experiment results wherein chondrocyte adhesion is the greatest on the conventional substrates compared to nano dimensional substrates, seeding density was at 5,000 cells/cm$^2$, values are mean +/− SEM, n=3, * $p<0.05$ (compared to cell density on respective non-aligned PLGA), ** $p<0.01$ (compared to cell density on aligned conventional substrate)

The present study showed the largest number of chondrocytes on the conventional substrates after 4-hour adhesion experiments, which is in contrast to a previous study [reference is made to Kay S, Thapa A, Haberstroh K M, and Webster T J, "Nanostructured Polymer/Nanophase Ceramic Composites Enhance Osteoblast and Chondrocyte Adhesion," *Tissue Engineering*, in press, 2002, which is hereby incorporated by reference herein]. This may be due to differences in population numbers or seeding density, since the previous study was done at lower seeding density and lower population numbers (1-5). As for the differences in aligned versus non-aligned substrates, more chondrocytes adhered to the aligned substrates compared to the non-aligned samples as shown in FIG. 2.

Figure 3:
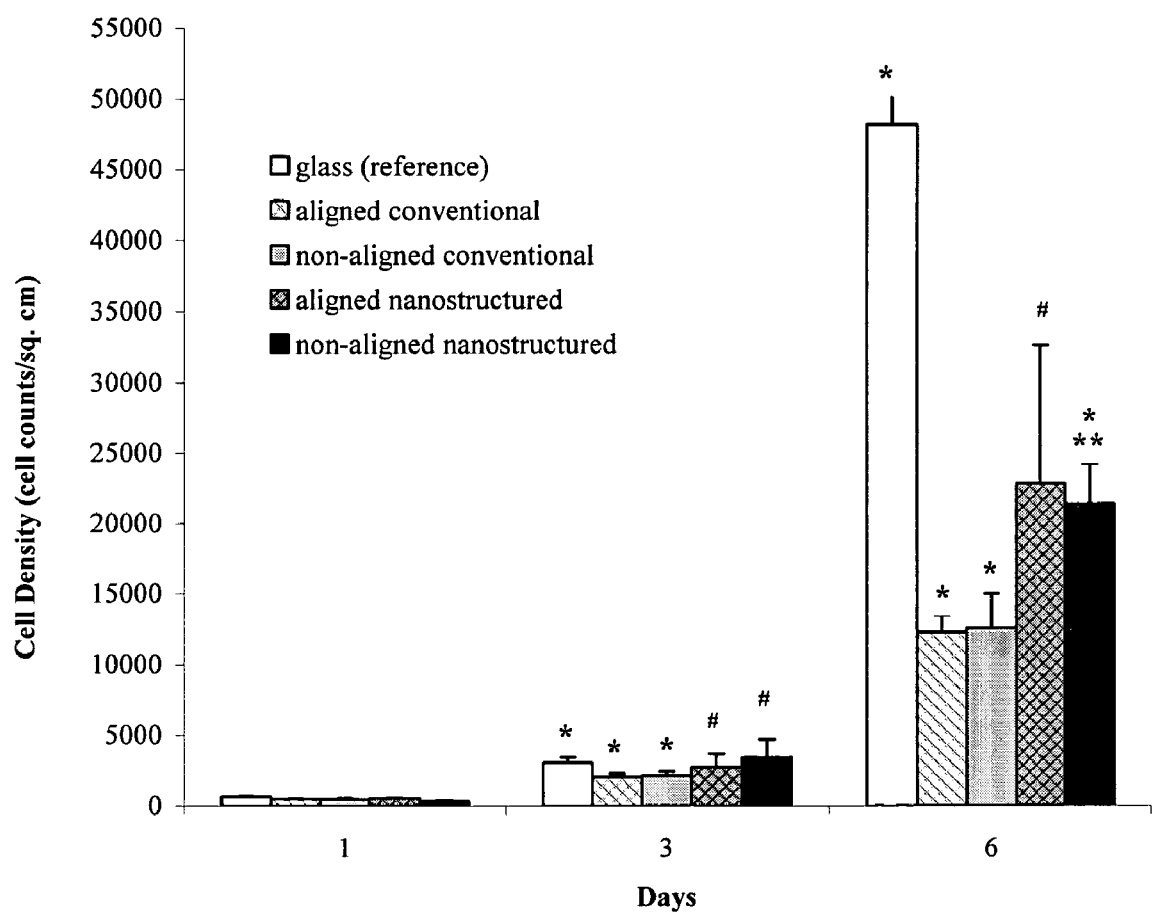
FIG. 3 shows 1, 3, and 6-day proliferation experiment results wherein chondrocytes in chondrocyte growth media were seeded (5,000 cells/cm$^2$) onto reference glass and PLGA substrates as described in section Materials and Methods and cultured for 1, 3, and 6 days, the number of chondrocytes was higher on nanostructured PLGA, Compared to conventional (micron-sized) controls, nanostructured substrates have more affinity to chondrocytes, values are mean +/− SEM, n=3, * $p<0.05$ (compared to cell density at day 1 on respective substrate), ** $p<0.05$ (compared to cell density on conventional PLGA substrates), # $p<0.1$ (compared to cell density at day 1 on respective substrate)

The results of the 1, 3, and 6-day proliferation experiments indicated that the chondrocyte proliferation rate increased on nanostructured substrates compared to the conventional samples. FIG. 3 displays the increased cell numbers on nanostructured samples. In contrast to the adhesion data, significant cell count differences were not seen between aligned and non-aligned substrates.

Chondrocyte migration study was performed to determine the distance the cells spread for 2, 4, and 6 days on each of the substrates previously described. The results are displayed in FIG. 4 below. The longer distances were obtained on nanostructured versus conventional PLGA, and the same trend was observed on aligned versus nonaligned substrates.

DISCUSSION AND CONCLUSIONS

Figure 4:
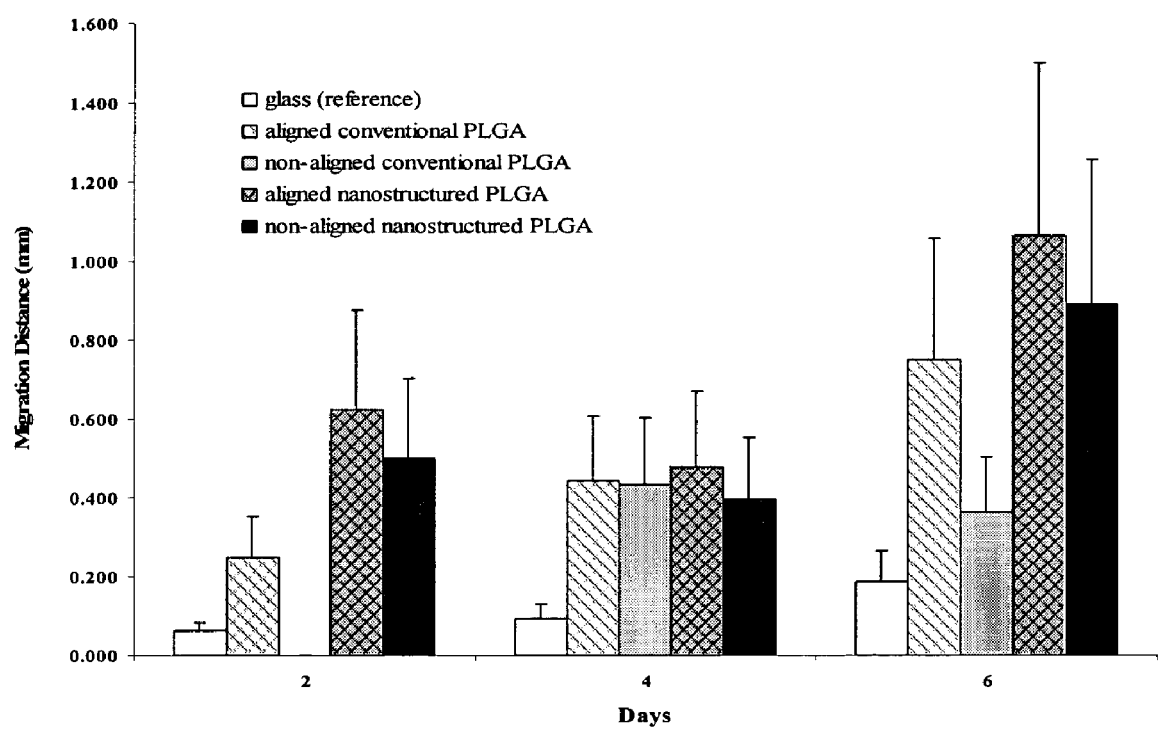
FIG. 4 shows increased migration distances on nano-structured and aligned PLGA wherein chondrocytes were allowed to adhere on the substrates of interest for 4 hours in the presence of TEFLON® inserts, TEFLON® fences were subsequently removed and cells were allowed to migrate for 2, 4, and 6 days, migration distance across the surfaces were determined at the end of each time period, and results are based on two separate experiments of triplicate samples.

Adhesion results from the present study demonstrated lower initial cell density on nano-dimensional substrates. However, increasing surface roughness (FIG. 1) enhanced the proliferation of chondrocytes according to the present study (FIG. 3). This indicates that the proliferation rate is higher on nanostructured substrates compared to the conventional samples, which implies the possibility of enhanced cartilage regeneration. This is further evidenced by the migration distances of chondrocytes from the 2, 4, and 6-day experiments which showed that chondrocytes tend to migrate faster on aligned and nanostructured substrates (FIG. 4).

In proliferation experiments, no difference in cell counts was observed between cells on aligned and on non-aligned substrates. However, in the presence of grooves or local alignment, chondrocytes grew along the direction of alignment (reference is made to Park G E, Savaiano J K, Park K, Webster T J, "An In Vitro Study of Chondrocyte Function on Nanostructured Polymer/Ceramic Formulations to Improve Cartilage Repair," *NANO2002 Conference Abstract Book*, Orlando, Fla., pg. 269, 2002, the disclosure of which is hereby incorporated by reference herein). One possible explanation for this phenomenon is that due to the presence of grooves and protrusion on the surface, proteins from the cell culture media interacted more favorably with aligned nano-structures to promote cell spreading. Since proteins are nanostructured (most <100 nm), their adsorption and conformation may be influenced to a larger degree on surfaces with nanometer (<100 nm) compared to conventional features. Another reason may be the chemical changes on the surface due to the etching process. However, previous studies have shown that when isolating surface topography from chemical etching changes in PLGA, bladder and vascular cells prefer the nanostructured compared to the conventional surface features (reference is made to Thapa A, Webster T J, and Haberstroh K M, "An Investigation of Nano-Structured Polymers for Use as Bladder Tissue Replacement Constructs," *Materials Research Society Symposium Proceedings* 711:GG3.4.1-GG3.4.6, 2002, and is made to Miller D M, Thapa A, Haberstroh K M, and Webster T J, "An In Vitro Study of Nano-Fiber Polymers for Guided Vascular Regeneration," *Materials Research Society Symposium Proceedings* 711:GG3.2.1-GG3.2.4, 2002, the disclosures of which are hereby incorporated by reference herein). Therefore, it is reasonable to speculate that alignment of nanostructured PLGA surface features alone serves to spatially control chondrocyte proliferation. The fact that the effect is long-term suggests that the cells can anchor well due to mechanical interlocking through the protein layer that may more tightly adsorb to the nanometer rough surface.

In summary, the results of the present study have shown a potential for modifying biodegradable polymer surface characteristics by creating aligned, nanometer features to enhance chondrocyte growth for articular cartilage repair.

The invention claimed is:

1. A substrate for promoting growth of chondrocytes to repair articular cartilage, the substrate comprising a polymeric material, wherein said polymeric material comprises aligned and nano-sized surface structures formed on the surface of said polymeric material of said substrate, said nano-sized surface structures comprising grooves and protrusions, wherein the grooves have a maximum depth, and the protrusions have a maximum height, of less than 100 nm.

2. The substrate of claim 1, wherein the polymeric material comprises poly(lactic/glycolic acid).

3. The substrate of claim 1, wherein the polymeric material is biodegradable.

4. The substrate of claim 1, wherein the polymeric material comprises a polymeric film.

5. The substrate of claim 1, wherein the polymeric material comprises a biodegradable poly(lactic/glycolic acid) film.

6. The substrate of claim 1, comprising a population of chondrocytes introduced on the surface of the polymeric material.

7. The substrate of claim 1, comprising chondrocytes grown along the aligned surface structures.

8. A substrate comprising a polymeric material with nano-sized surface structures, wherein a dimension of the nano-sized surface structures is less than 100 nm, said dimension selected from the group consisting of cross-sectional diameter and height.

9. The substrate of claim 8, wherein the surface structures comprise aligned grooves and protrusions.

10. A substrate comprising a polymeric material wherein the surface of said polymeric material comprises nano-sized protrusions and grooves, wherein a dimension of said protrusions and grooves is less than 100 nm.

11. The substrate of claim 10, wherein the polymeric material surface comprises a biodegradable poly(lactic/glycolic acid) film, said film further comprising a population of chondrocytes introduced on the biodegradable poly (lactic/glycolic acid) film.

12. The substrate of claim 10 wherein the nano-sized protrusions and grooves are aligned.

* * * * *